(12) United States Patent
Heyes et al.

(10) Patent No.: US 10,456,516 B2
(45) Date of Patent: *Oct. 29, 2019

(54) DIALYSIS MACHINE

(71) Applicant: Quanta Dialysis Technologies Limited, Warwickshire (GB)

(72) Inventors: Keith James Heyes, Worcestershire (GB); Hugh Christopher Bramley, Oxon (GB); Mark Reeves, Oxford (GB); Mark Jervis, Merseyside (GB)

(73) Assignee: Quanta Dialysis Technologies Limited, Warwickshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,501

(22) Filed: Oct. 12, 2017

(65) Prior Publication Data

US 2018/0154059 A1 Jun. 7, 2018

Related U.S. Application Data

(63) Continuation of application No. 15/604,491, filed on May 24, 2017, now abandoned, which is a (Continued)

(30) Foreign Application Priority Data

| May 6, 2005 | (GB) | .................................. | 0509330.7 |
| Sep. 7, 2005 | (GB) | .................................. | 0518175.5 |
| Feb. 24, 2006 | (GB) | .................................. | 0603729.5 |

(51) Int. Cl.
*A61M 1/16* (2006.01)
*A61M 1/36* (2006.01)
(Continued)

(52) U.S. Cl.
CPC ............ *A61M 1/1635* (2014.02); *A61M 1/16* (2013.01); *A61M 1/1694* (2013.01);
(Continued)

(58) Field of Classification Search
CPC .... A61M 1/16; A61M 1/1635; A61M 1/1694; A61M 1/3627; A61M 1/3663; A61M 1/3672; A61M 2205/123; A61M 2205/3306; A61M 2205/3375; A61M 2205/3382; A61M 2205/3386; A61M 1/1696; B01D 2313/44; B01D 61/243; B01D 61/28; B01D 61/30; B01D 63/06
See application file for complete search history.

(56) References Cited

U.S. PATENT DOCUMENTS

| 5,421,823 A * | 6/1995 | Kamen | .................... A61M 1/28 |
| | | | 210/929 |
| 2004/0206703 A1 * | 10/2004 | Bosetto | ............... A61M 1/1656 |
| | | | 210/634 |
| 2005/0020961 A1 * | 1/2005 | Burbank | .................. A61M 1/34 |
| | | | 604/4.01 |

* cited by examiner

*Primary Examiner* — John Kim
(74) *Attorney, Agent, or Firm* — Cooley LLP

(57) ABSTRACT

A disposable cartridge for use in a hemodialysis machine has a blood flow path for carrying a volume of blood to be treated in a dialyser and a dialysate flow path, isolated from the blood flow path, for delivering a flow of dialysate solution through the dialyser. The cartridge is received in an engine section of the machine. The engine section has first and second platens which close when the cartridge is inserted to retain the cartridge. Actuators and sensors arranged on the second platen control operation of the cartridge.

4 Claims, 15 Drawing Sheets

Figure 1:
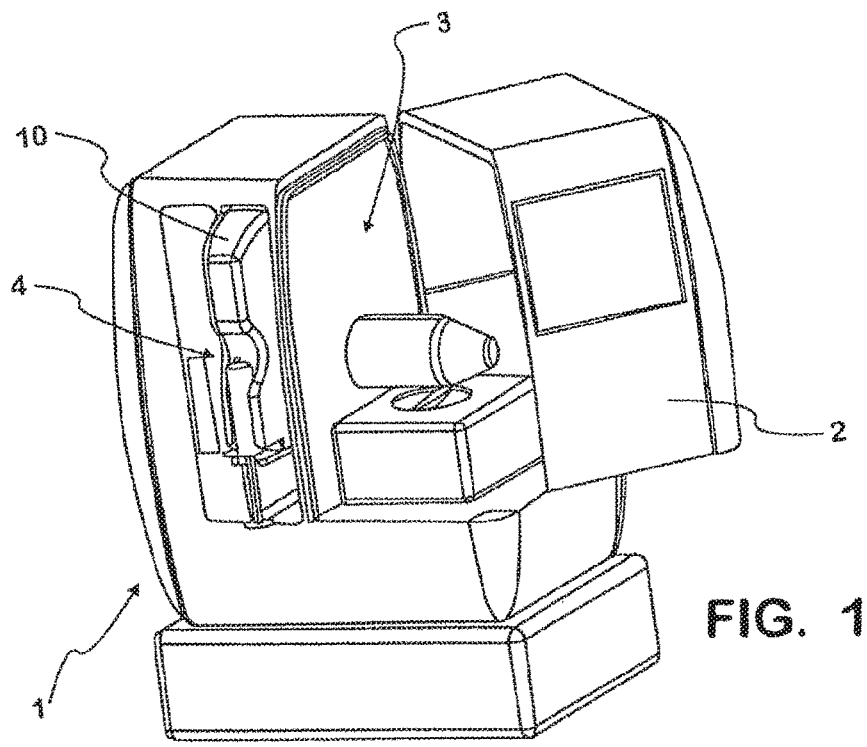

Related U.S. Application Data continuation of application No. 14/195,601, filed on Mar. 3, 2014, now abandoned, which is a continuation of application No. 13/488,830, filed on Jun. 5, 2012, now Pat. No. 8,685,244, which is a continuation of application No. 12/460,427, filed on Jul. 17, 2009, now abandoned, which is a continuation of application No. 11/919,694, filed as application No. PCT/GB2006/001668 on May 8, 2006, now abandoned.

(51) Int. Cl.
*B01D 61/24* (2006.01)
*B01D 61/28* (2006.01)
*B01D 61/30* (2006.01)
*B01D 63/06* (2006.01)

(52) U.S. Cl.
CPC ........ *A61M 1/1696* (2013.01); *A61M 1/3627* (2013.01); *A61M 1/3672* (2013.01); *B01D 61/243* (2013.01); *B01D 61/28* (2013.01); *B01D 61/30* (2013.01); *B01D 63/06* (2013.01); *A61M 1/3663* (2013.01); *A61M 2205/123* (2013.01); *A61M 2205/3306* (2013.01); *A61M 2205/3334* (2013.01); *A61M 2205/3375* (2013.01); *A61M 2205/3382* (2013.01); *A61M 2205/3386* (2013.01); *B01D 2313/44* (2013.01)

DIALYSIS MACHINE

The present application is a continuation of U.S. patent application Ser. No. 15/604,491, filed on May 24, 2017 (abandoned), which is a continuation of U.S. patent application Ser. No. 14/195,601, filed on Mar. 3, 2014 (abandoned), which is a continuation of U.S. patent application Ser. No 13/488,830, filed Jun. 5, 2012 (issued as U.S. Pat. No. 8,685,244), which is a continuation of U.S. patent application Ser. No. 12/460,427, filed on July 17, 2009 (abandoned), which is a continuation of U.S. patent application Ser. No. 11/919,694, filed Oct. 31, 2007 (abandoned), which is a U.S. national stage of international patent application no. PCT/GB2006/001668, filed on May 8, 2006, which claimed the benefit of the filing dates of GB0603729.5, filed Feb. 24, 2006; GB0518175.5, filed Sep. 7, 2005; and GB0509330.7, filed May 6, 2005. The contents of each of the above disclosures are incorporated herein by reference in their entireties.

The present invention relates to dialysis machines and in particular, but not exclusively, to a disposable cartridge for use in hemodialysis machine.

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line, is treated by the dialysis machine, and is then returned to the body by a venous line. The machine passes the blood through a dialyser containing tubes formed from a semipermeable membrane. On the exterior of the semipermeable membrane is a dialysate solution. The semipermeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by altering the hydrostatic pressure of the dialysate side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysis solution consists of a sterilized solution of mineral ions. These ions are contained within an acid buffer which is mixed with the serialized water and bicarbonate base prior to delivery to the dialyser.

Dialysate composition is critical to successful dialysis treatment since the level of dialytic exchange across the membrane, and thus the possibility to restore adequate body electrolytic concentrations and acid-base equilibrium, depends on the composition.

The correct composition is accomplished primarily by formulating a dialysate whose constituent concentrations are set to approximate normal values in the body.

However, achieving the correct composition of dialysate requires the accurate control of low volumes of liquid and at present this is achieved by the provision of complex fluid paths, including multiple pumping and valving components on the dialysis machine.

This presents the disadvantage of a complex and costly dialysis machine which is at increased risk of failure by virtue of its complexity. Increased maintenance is also a problem since it is essential to minimize machine downtime in order to most efficiently treat the patient.

A further problem with known hemodialysis machines is that the blood and dialysate solution lines require careful mounting onto the dialysis machine before the treatment can commence. This presents a risk that the lines are not correctly installed, a risk which is particularly relevant to those patients who dialyse at home.

This method of dialysis also presents an increased risk of cross-infection between patients since the disposable blood and dialysate lines come into contact with the dialysis machine.

It is an object of the present invention to provide a hemodialysis system which at least mitigates some of the problems described above.

According to a first aspect of the invention there is provided a disposable cartridge for use in a hemodialysis machine, the cartridge comprising a blood flowpath for carrying a recirculating volume of blood to be treated in a dialyser and a dialysate flowpath, isolated from the blood flowpath, for delivering a flow of dialysate solution through the dialyser.

Preferably, the cartridge has a first mixing pump and a second mixing pump, the second mixing pump accepting a homogeneous mix of sterile water and a first dialysate solution base from the first mixing pump and introducing a further dialysate solution base.

Preferably, the dialysate pathway includes a first three-way valve upstream of the first dialysate solution mixing pump, the first three-way valve controlling delivery of the first dialysate solution base into the first mixing pump.

Preferably, the first three-way valve has a mixing pump outlet port, a dialysate solution reservoir inlet port and a positive displacement pump port.

Preferably, the first three-way valve acts to permit a volume of a first dialysate solution base into the first dialysate solution mixing pump on each and every stroke of the pump.

Preferably, the dialysate pathway includes a second three-way valve upstream of the second dialysate solution mixing pump.

Preferably, the cartridge includes a dialysate solution reservoir, more preferably a first reservoir immediately downstream of the first mixing pump and a second reservoir immediately downstream of the second mixing pump.

Preferably, the blood and dialysate fluid pathways pass between a first outwardly facing surface of the cartridge and a second outwardly facing surface of the cartridge.

Preferably, at least some parts of the first and second outwardly facing surfaces of the cartridge body are covered with a deformable membrane.

Preferably, the valves and pumps on the cartridge are actuable by deformation of the membrane by the dialysis machine.

Preferably, the blood and dialysate solution fluid pathways are at least partially defined by upwardly standing walls projecting outwardly from the upper and lower surfaces of the cartridge.

Preferably, the upstanding walls are enclosed by the deformable membranes.

Preferably, the mixing pumps are membrane pumps.

Preferably, the blood flow path is provided with at least one blood bubble trap, more preferably, the or each blood bubble trap is provided with a level sensor.

Preferably, the level sensor is an optical level sensor, or an ultrasonic level sensor.

Preferably, the blood bubble trap is provided with an upper and a lower level sensor.

Preferably, the blood bubble trap is provided with a hydrophilic membrane for removing or adding a volume of air to the blood bubble trap.

Preferably, the cartridge is provided with a positive displacement pump plunger acting in combination with the three-way valve to deliver a measured volume of dialysate solution base into the dialysate solution mixing pumps.

Preferably, the cartridge is provided with an endotoxin filter, preferably a single use endotoxin filter.

Preferably, the dialysate solution fluid pathway is provided with an ultra-sonic flow sensor for detecting the flow rate through the dialysate solution path.

Preferably, the cartridge defines a series of apertures interlinking the portion of fluid pathways defined on the upper surface of the cartridge with the portion of fluid pathways defined on the lower surface of the cartridge.

According to a second aspect of the invention there is provided a dialysis machine adapted to receive the dialysis cartridge of the first aspect of the invention, the machine including at least one platen arranged in use to hold the cartridge in position on the machine.

Figure 2:
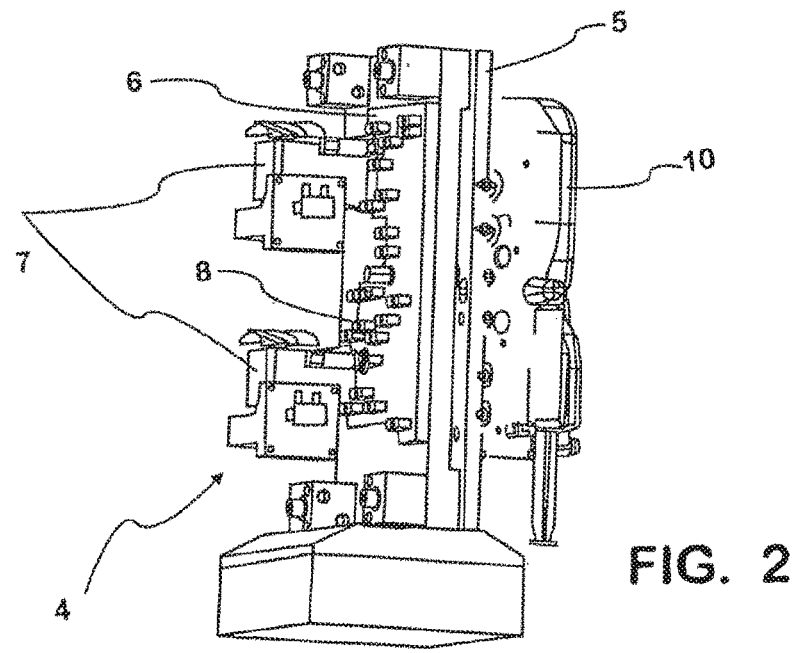
Figure 3:
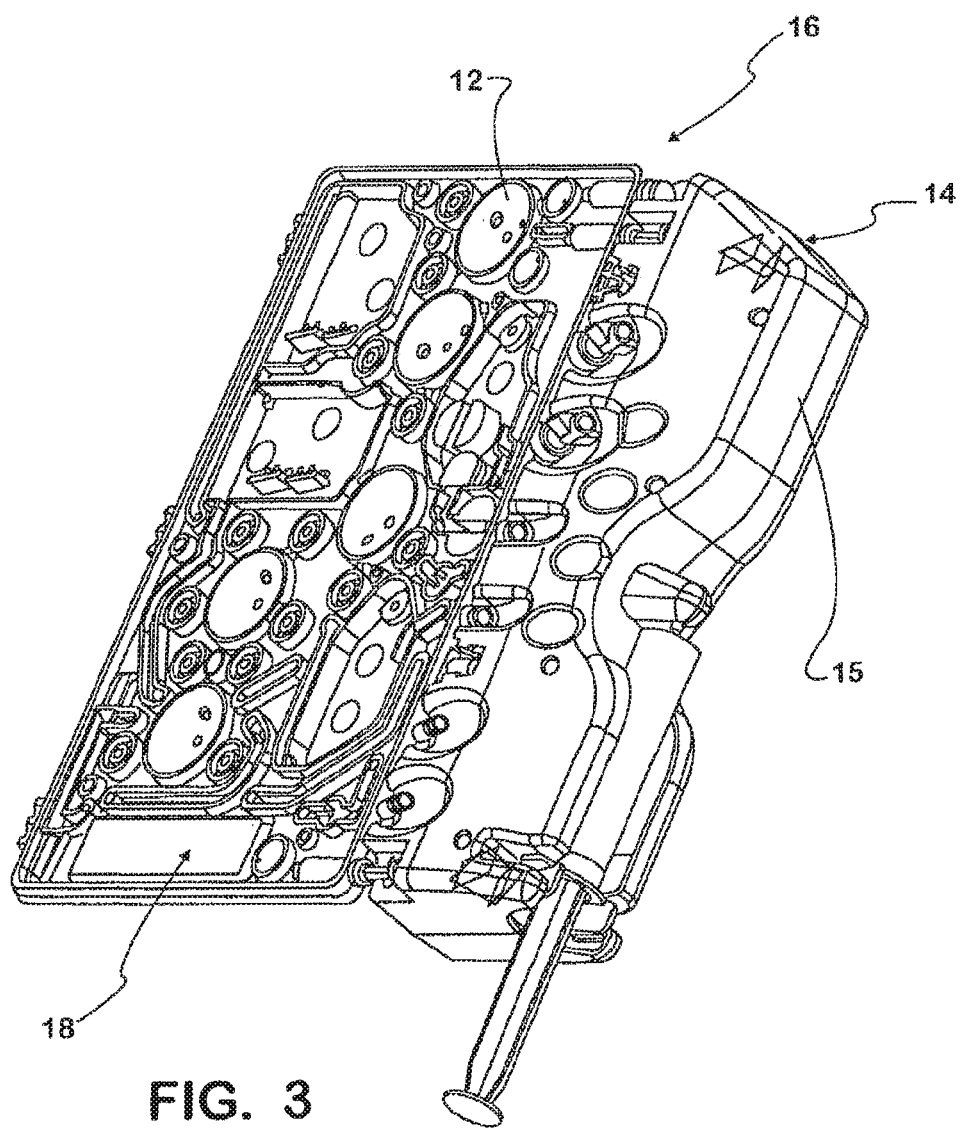
Figure 4:
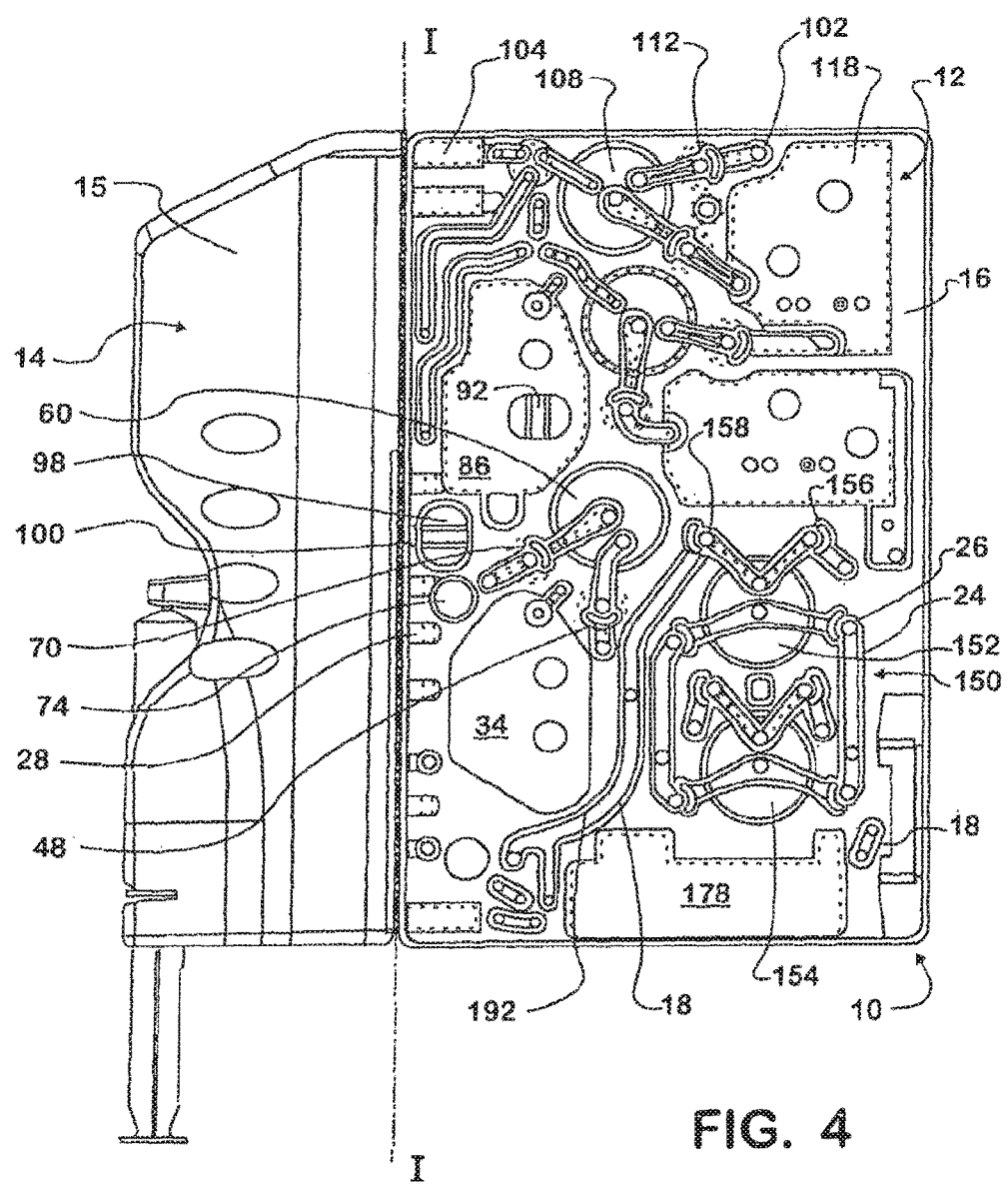
Figure 5:
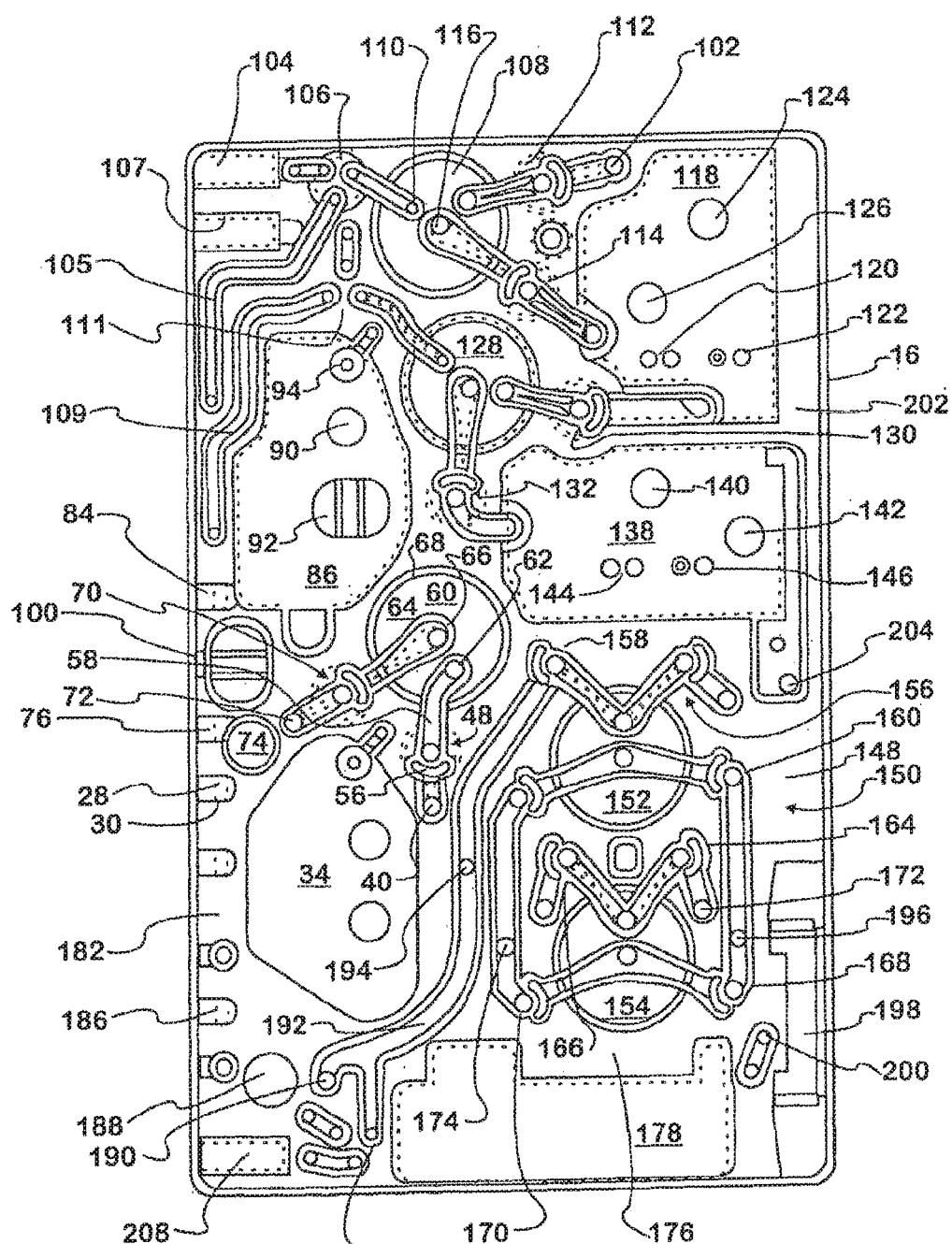
Figure 6:
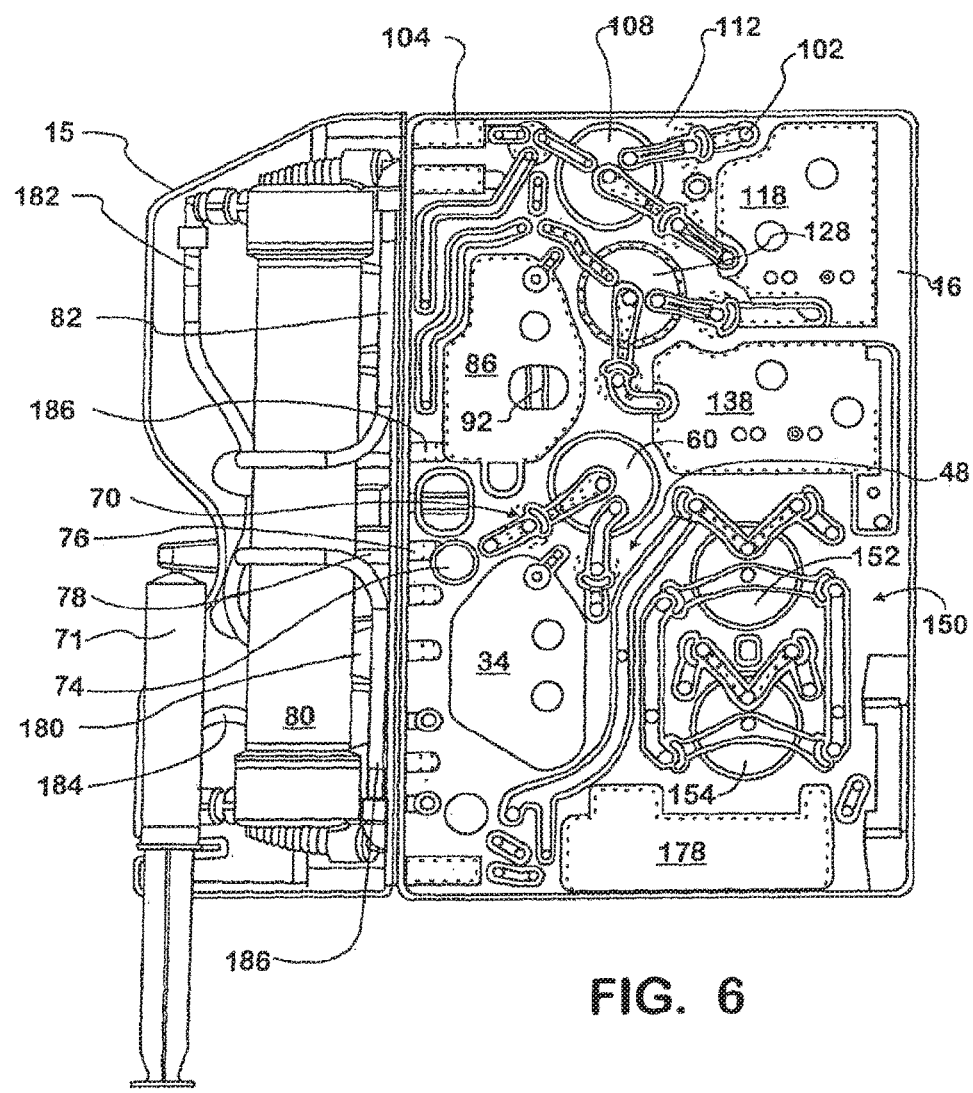
Figure 7:
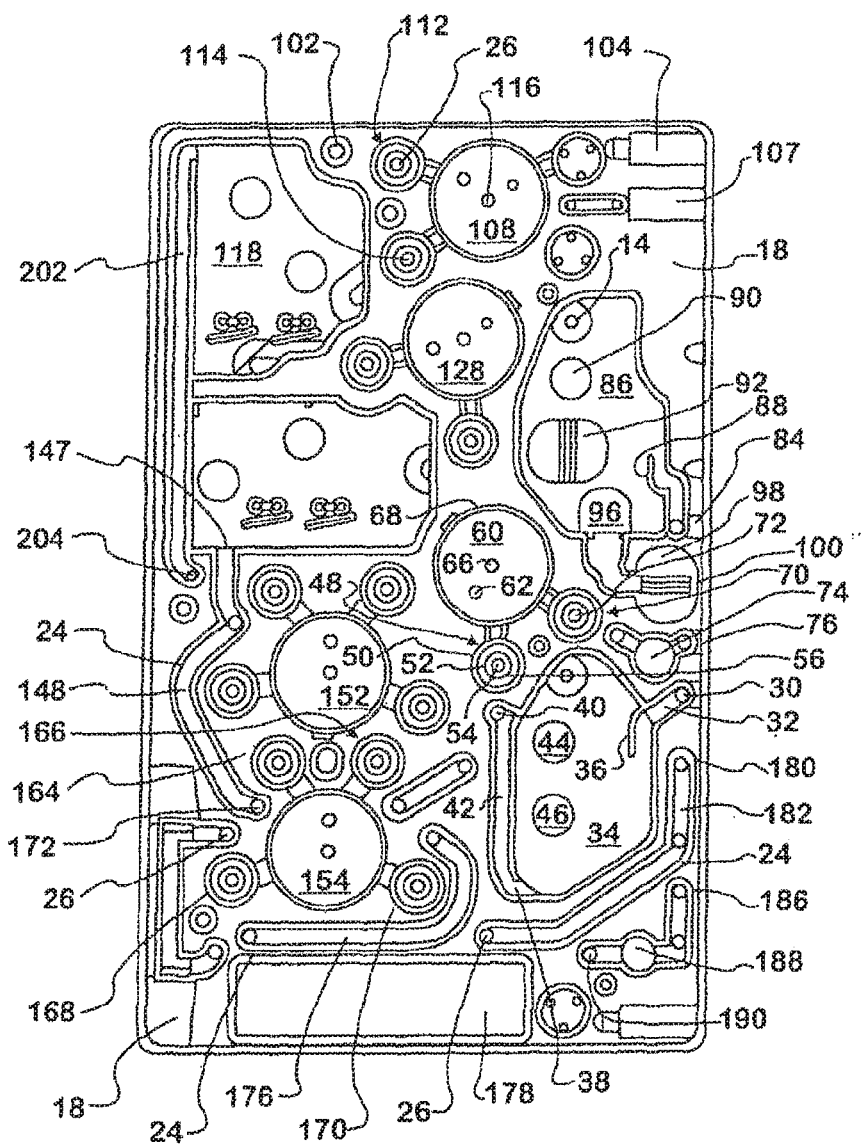
Figure 8:
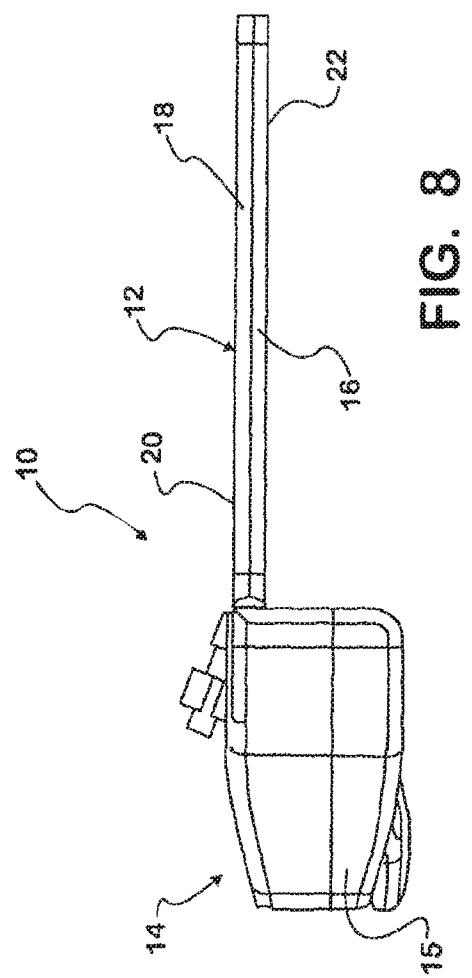
Figure 9:
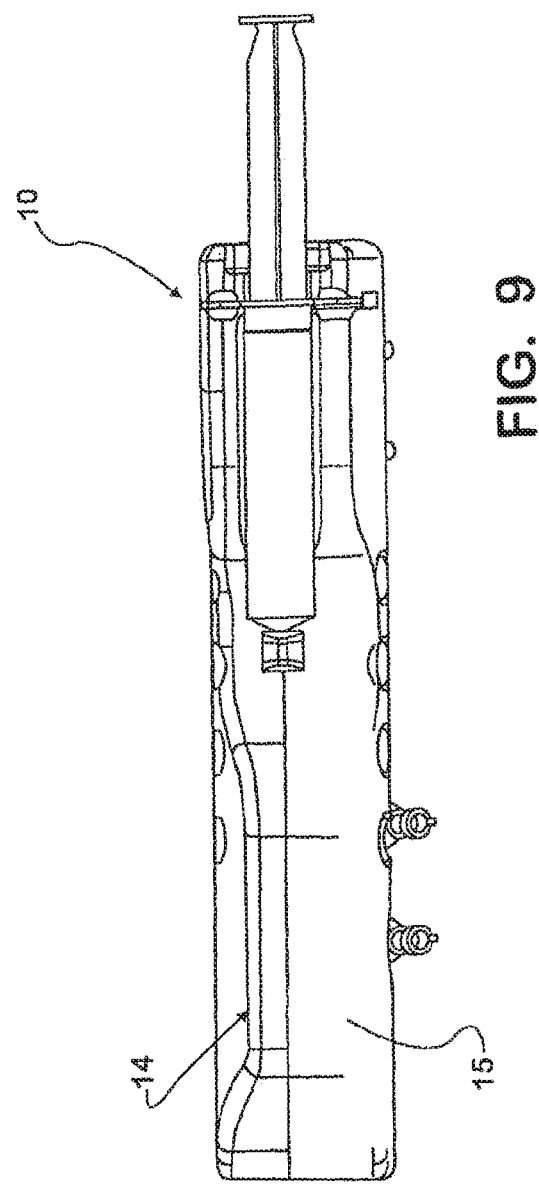
Figure 10:
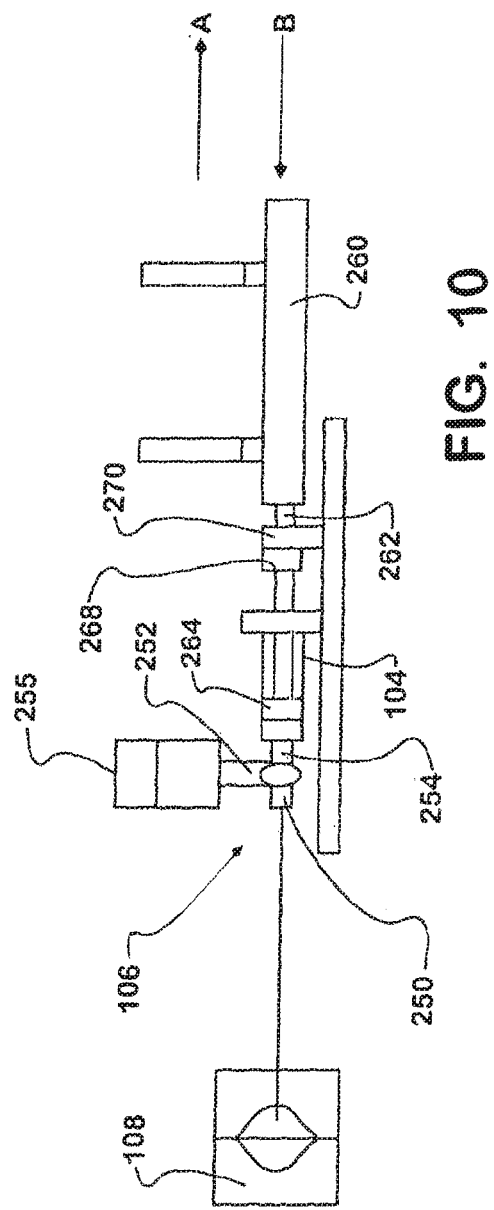
Figure 11:
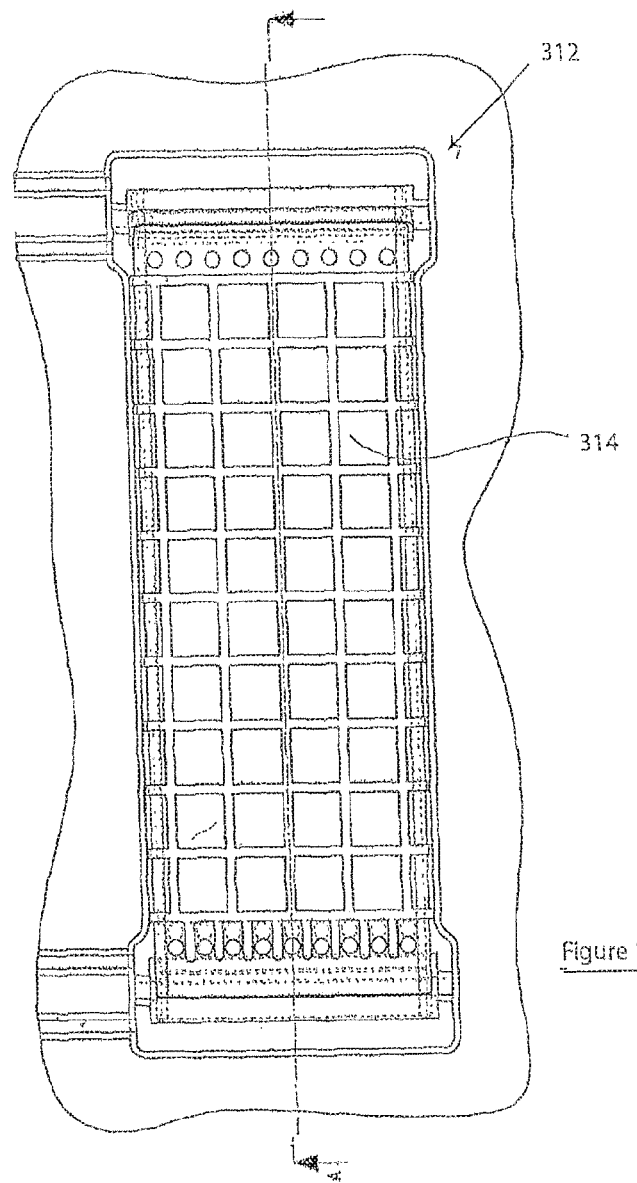
Figure 12:
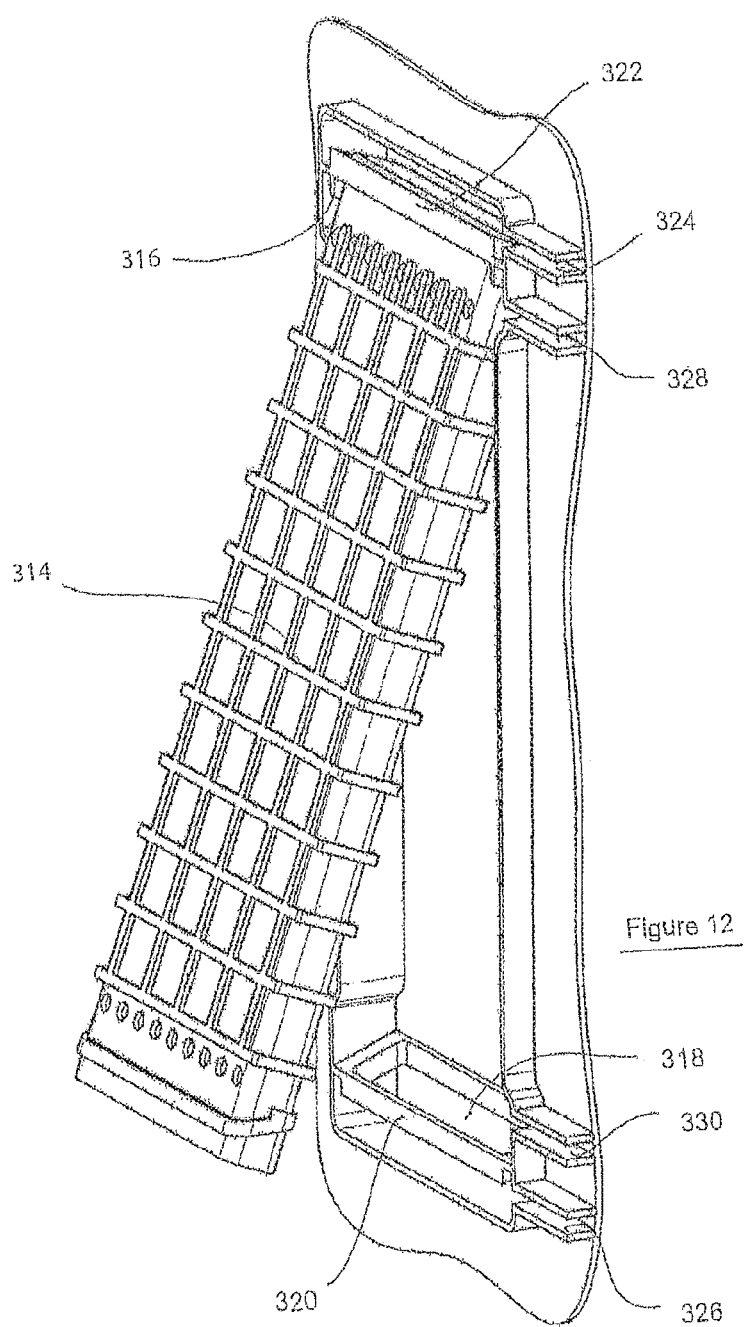
Figure 13:
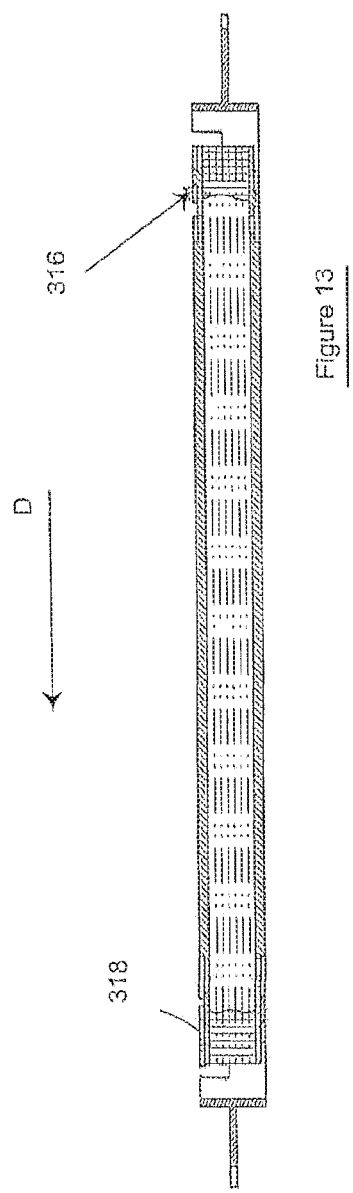
Figure 14:
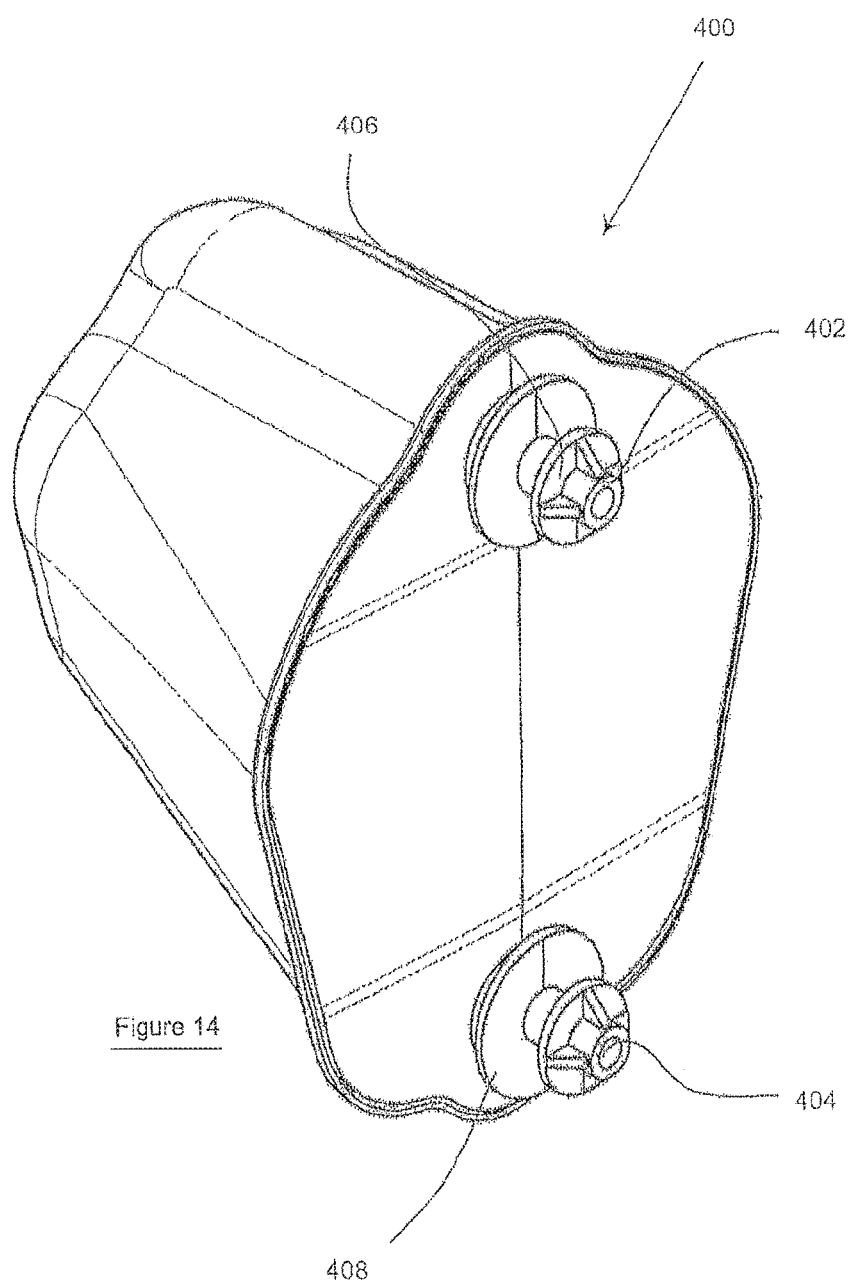
Figure 16:
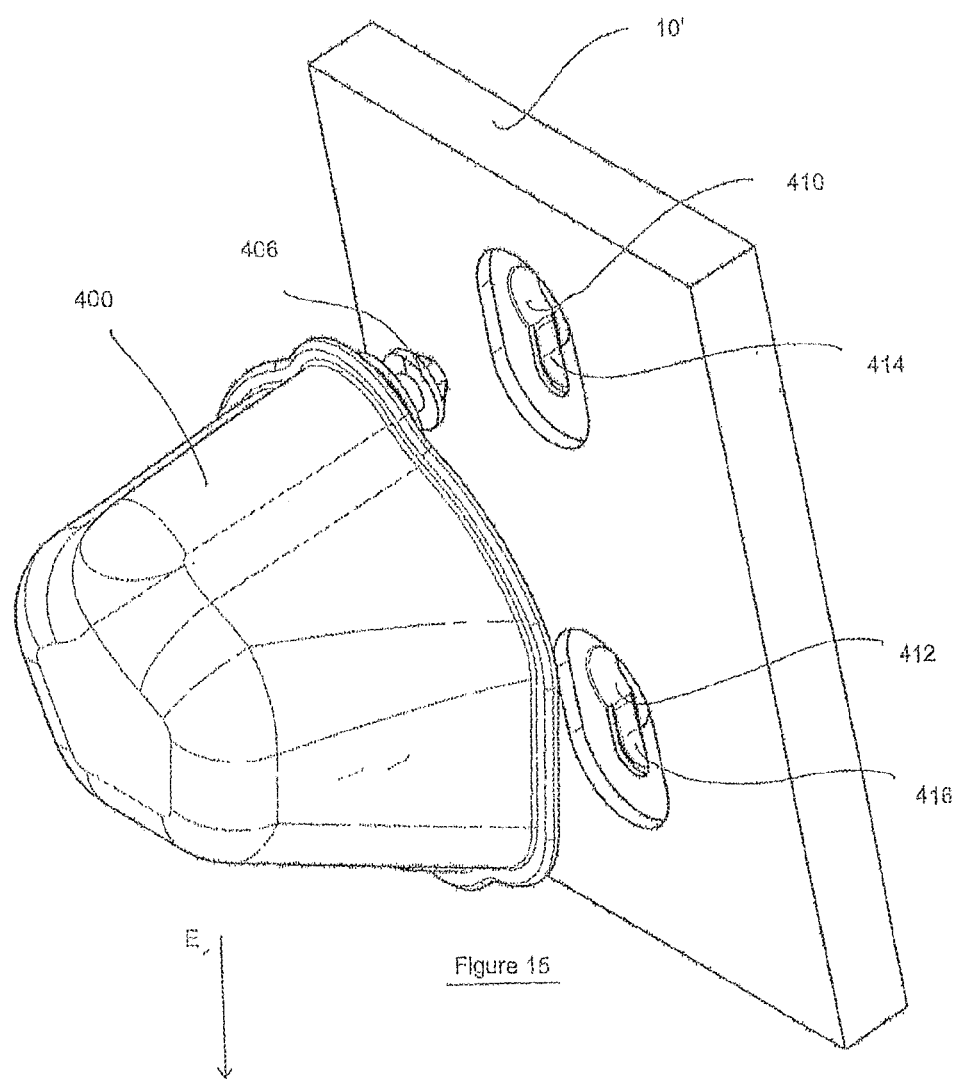
Figure 16:
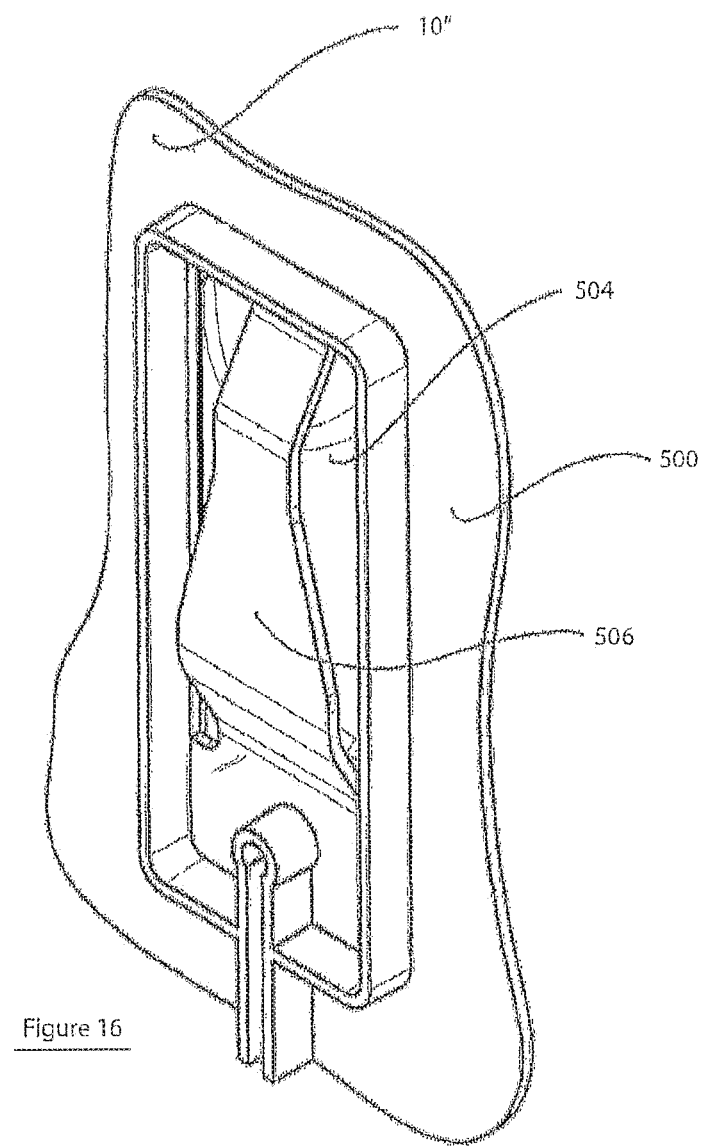

The invention will now be described, by way of example only, and with reference to the following drawings, in which:

FIG. 1 is an isometric view of the dialysis machine and cartridge of the current invention, FIG. 2 is an isometric view of the engine portion of the machine of FIG. 1, FIG. 3 is an isometric view of the cartridge of the present invention, FIG. 4 is a front view of the cartridge of FIG. 3, FIG. 5 is a front view of the pumping portion of the cartridge of FIG. 3 showing partial hidden detail, FIG. 6 is a front view of the cartridge of FIG. 3 showing the dialyser cover removed, FIG. 7 is a rear view of the pumping portion of the cartridge of FIG. 3, FIG. 8 is a top view of the cartridge of FIG. 3, FIG. 9 is an end view of the cartridge of FIG. 3, and FIG. 10 is a schematic representation of a dialysate solution base delivery system according to the present invention, FIG. 11 is a partial plan view of an alternative embodiment of cartridge of the present invention with a dialyser integral to the cartridge, FIG. 12 is a partial isometric view of the alternative cartridge of FIG. 11, FIG. 13 is a side view of the the alternative cartridge of FIG. 11, FIG. 14 is an isometric view of a bicarbonate cartridge according to the present invention, FIG. 15 is an isometric view of the bicarbonate cartridge of FIG. 14 shown in association with a partial view of an alternative embodiment of cartridge, and FIG. 16 is a partial isometric view of an alternative embodiment of cartridge according to the present invention showing an anticoagulant reservoir.

In FIG. 1 a dialysis machine 1 is shown having a cover 2 which opens to reveal a storage compartment 3. The machine has an engine section 4 which receives a dialysis cartridge 10.

Referring now to FIG. 2, the engine section 4 is shown in further detail to include first and second platens 5, 6 which close upon insertion of the cartridge 10 into the machine to retain the cartridge in position in use. The engine 4 has pneumatic actuators 7 and sensors (indicated generally at 8 in FIG. 2) arranged on the second platen to control operation of the cartridge 10 as will be described in further detail shortly.

In FIGS. 3 and 4 a dialysis cartridge 10 is shown having a pumping portion 12 (to the right of dashed line I-I in FIG. 4) and a dialysis portion 14 (to the left of dashed line I-I in FIG. 4). The pumping portion 12 has the form of a flat rectangle. The dialysis portion 14 has a dialyser cover 15 which is shaped so as to contain a dialyser as will be described in further detail shortly.

Referring briefly to FIG. 8, the pumping portion 12 of the dialysis cartridge 10 has an upper surface 16 and a lower surface 18. The upper surface 16 and a lower surface 18 are covered by a clear membrane 20, 22, respectively, which is formed from a deformable plastics material. The first and second membrane, 20, 22 are bonded to the upper surface 16 and a lower surface 18, respectively by way of adhesive or similar known method.

Referring now to FIG. 4, the upper surface 16 defines a series of upstanding walls indicated, for example, as 24. The upstanding walls 24 define a system of flow channels as will be described in further detail shortly. The channels are enclosed at the outermost part of the upper surface 16, by the first membrane 20. Accordingly, the upper surface 16 defines a series of fluid channels for carrying either the blood to be dialysed, or the Dialysate solution.

The cartridge 10 also defines the series of apertures, indicated generally for example at 26 in FIG. 4. These apertures provide a fluid pathway through the cartridge 10, the purpose of which will now be described.

Referring to FIG. 7, the lower surface 18 also defines a series of upstanding walls 24, which collectively define a labyrinth of fluid channels enclosed by the second membrane 22.

In combination therefore the upper surface 16, lower surface 18 and the first and second membranes 20, 22 form a series of interconnected fluid flow paths on both sides of the pumping portion 12. This labyrinth of fluid flowing pathways will now be described in further detail.

The first membrane 20 is bonded to the upper surface 16, and similarly the second membrane 22 bonded to the lower surface 18, so as to contain the fluids within their respective channels.

The dialyser cartridge 10 defines two primary fluid pathways, firstly, a flow path for blood and secondly a flow path for the dialysate solution. The blood pathway, is formed as follows.

The patient's blood enters the dialysis cartridge 10 via an arterial port 28. The blood then passes from the upper surface 16 to the lower surface 18 via an arterial port aperture 30 where it is then carried by an arterial port channel 32 from the arterial aperture 30 to an arterial blood bubble trap 34. The arterial blood bubble trap 34 has an inlet lip 36 for directing the incoming blood towards the bottom of the trap. Arranged at the bottom of the trap is a blood bubble trap exit 38 which carries the blood from the arterial blood bubble trap 34 to an arterial blood bubble trap aperture 40 via channel 42.

The purpose of the arterial blood bubble trap 34 is to remove from the arterial blood supply any gas bubbles which may be contained therein. Gas bubbles may impair the performance of dialyser, and furthermore, present a risk to the patient if they were reintroduced back into the body via the venous blood line. The blood bubble trap 34 is also provided with an upper level sensor port 44 and a lower level sensor port 46. The level sensor ports 44, 46 are arranged to coincide with corresponding optical level sensors arranged on the dialysis machine. Accordingly, the level sensors are able to optically interrogate the arterial blood bubble trap 34 so as to ensure that the level in the blood bubble trap is above the level of the lower level sensor port 46 and below the level of the upper level sensor port 44. It is important to ensure that the blood level remains between these two levels so that there always remains a volume of air in the blood level trap into which any gas bubbles carried it the blood can migrate.

Having passed through the arterial blood bubble trap aperture 40 the blood is carried on the upper surface 16 to a blood pump inlet valve 48 (see FIG. 4).

Referring to FIG. 4, the blood pump inlet valve 48 is operable between a closed condition and an open condition as follows. The valve 48 has an outer annular upstanding wall 50 and an inner annular upstanding wall 52. Arranged inwardly of the inner upstanding annular wall 52 is a valve aperture 54. The inner upstanding annular wall 52 is recessed from the outer upstanding annual wall 50 in a direction towards the cartridge 10. Arranged between the inner and outer upstanding annual wall 50, 52 is a sector aperture 56 which acts as an outlet from the valve 48. Accordingly, the valve 48 has a valve inlet in the form of valve aperture 54 and an outlet in the form of the sector aperture 56. As discussed previously, the lower surface 18 has its outer service covered by a deformable membrane 22. The deformable membrane 22 rests against the outwardly facing surface of the outer upstanding annular wall 50 where the valve is in the un-actuated, open state. In order to change the condition of the valve 48 from the open state to the closed state, the dialysis machine applies a positive pressure to the exterior surface of the second membrane 22 in order to drive the inner surface of the membrane on to the outwardly facing surface of the inner upstanding annular wall 50. This closes the inlet to the valve thereby preventing flow through the valve.

With the blood pump inlet valve 48 in the open state, the blood flows through the arterial blood bubble trap aperture 40 over the inner upwardly standing wall 50 and through the sector aperture 56 so as to exit the blood pump inlet valve 48. From the sector aperture 56 the blood then flows down a blood pump inlet channel 58 and into a blood pump 60 via a blood pump inlet 62.

The blood pump is defined by a dome shaped pump cavity 64 into which the blood pump inlet 62 opens. Arranged at the centre of the pump chamber 64 is a pump outlet 66. The outer edge of the pump chamber 64 is defined by an annular upstanding wall 68, the outwardly facing surface of which is in contact with the inner surface of the second membrane 22. A volume of blood is drawn into the pump chamber 64, through the open blood pump inlet valve 48 as follows.

The dialysis machine generates a negative pressure on the outside surface of the second membrane 22 in order to deform the membrane outwardly away from the lower surface 18. With the pump chamber 64 full, and the pump at full stroke, the blood pump inlet valve 48 is closed by the dialysis machine generating positive pressure on the outside surface of the second membrane 22 in order to close the valve aperture 54. The pump chamber 64 is then evacuated by the dialysis machine applying a positive pressure to the outside surface of the second membrane 22 in order to drive the blood contained within the pump chamber 64 through the pump outlet 66. The pump outlet 66 is in fluid communication with a blood pump outlet valve 70 which is identical in form to the blood pump inlet valve 48. It follows that with the blood pump inlet valve closed, and the blood pump 60 being driven by the dialysis machine to evacuate the pump 64, the blood pump outlet valve 70 is in an open state in order to permit the flow of blood past the valve 70 and through a blood pump outlet valve aperture 72.

Accordingly, the blood pump 60 is in combination with the blood pump inlet valve 48 and the blood pump outlet valve 70. Specifically, the blood pump inlet valve 48 opens when the blood pump is in the expansion stroke in order to admit blood into the pump chamber, whilst the blood pump outlet valve 70 remains closed in order to prevent back-flow of blood through the system. The inlet valve 48 then closes at the same time as the outlet valve 70 is opened m order to allow the compression stroke of the flow pump to drive the blood from the pump chamber 64 and through the blood pump outlet valve aperture 72.

From the aperture 72, the blood then flows through a pressure sensor chamber 74. As the blood flows through the chamber 74, the fluid pressure causes a force to be applied to the first membrane 20 which in turn causes a deflection in the membrane. This deflection is detected by a sensor provided in the dialysis machine and this measured deflection is calibrated to generate a blood pressure reading for within the cartridge.

From the pressure sensor chamber 74 the blood then passes through a dialyser blood port 76.

Referring now to FIG. 6, the blood flows from the dialyser blood port 66 down a dialyser blood line 78 and into the bottom and of a dialyser 80 of known design. The dialyser 80 contains multiple axially extending semi-permeable tubes through which the blood passes. Upon exiting the dialyser 80 the blood travels down a dialyser return blood line 82 before passing into a venous blood bubble trap 86 via a dialyser blood return port 84.

The venous blood bubble trap 86 is similar in design to the arterial blood bubble trap 34 in that it has an inlet lip 88, an optical level sensor 90 and a hydrophilic membrane 94 to allow the hydrolysis machine withdraw or administer a volume of air to or from the bubble trap in order to maintain a constant blood level within the bubble trap. The venous blood level trap 86 is further provided with an ultrasonic level sensor 92 the design of which will be described in further detail shortly. At the bottom end of the valve trap is a thrombus filter 96 for trapping blood clots within the bubble trap. The Thrombus filter may be of conical form as in known thrombus filters or may be wedge shaped. Having passed through the thrombus filter 96, the blood passes through an ultrasonic flow rate sensor 98 which will be described in further detail shortly. The blood is then returned to the patient via a venous port 100.

The blood therefore completes its passage through the dialysis cartridge 10 from the arterial port 28 through the arterial blood bubble trap 34, the blood pump inlet valve 48 and into the blood pump 60. From blood pump 60 the blood is driven past the blood pump outlet valve 70 and into the dialyser 80 via the cross membrane pressure sensor 74. Upon exit from the dialyser 80, the blood is returned to the dialysis cartridge 10 via the dialyser blood return port 84. Upon exit from the port 84 the blood enters the venous blood bubble trap 86, passes through the thrombus filter 96 and flow sensor 98 before being returned to the patient via the venous port 100.

A syringe 71 is provided which introduces a volume of an anti-coagulant drug such as heparin into the blood line between the blood pump outlet valve 70 and the dialyser 80. The syringe plunger 73 is driven by the machine engine as shown in FIG. 2.

As described above, dialysis occurs across a semi-permeable membrane, in this instance the semi-permeable tubes provided within the dialyser 80. As described, the blood flows through the centre of the semi-permeable tubes and it therefore follow that the dialysate solution flows in the space within the dialyser 80 between the tubes. The mixing of the dialysate solution on the cartridge at the correct concentration will now be described in detail.

The pump portion 12 defines the dialysate flow path in addition to the blood flow path as described above.

Accordingly, the dialysis cartridge 10 provides for the mixing into a sterile water supply of a small volume of concentrated bicarbonate solution and a small volume of acid solution. The resulting dialysate solution is pumped from the pumping portion to deliver the solution to the dialyser. The cartridge further allows for the accurate sensing of dialysate solution concentration, dialysate flow rate and dialysate pressure.

Sterile water enters the dialysis cartridge 10 via a sterile water inlet 102. The sterile water is then mixed with a controlled volume of bicarbonate solution base as follows. The cartridge 10 defines a chamber 104, for receiving the plunger of a positive displacement pump (not shown for clarity in FIGS. 3 to 9). The pump acts in combination with a three-way valve 106 of known design. The pump and three-way valve 106 are operated by the dialysis machine to micro-dose a controlled volume of bicarbonate solution into a bicarbonate pump 108. The bicarbonate pump 108 is of similar design to the blood pump 60 with the exception that the bicarbonate pump 108 is additionally provided with an inlet 110 from the three-way valve 106. The bicarbonate pump 108 is controlled in exactly the same manner to the flow pump 60 in order to draw a volume of sterile water through the sterile port at 102 and past a bicarbonate inlet pump 112 whilst a bicarbonate pump outlet valve 114 remains closed. At the same time as a volume of sterile water is drawn into the pump a small volume of saturated bicarbonate solution is injected into the bicarbonate pump 108 by a positive displacement pump. The body of the positive displacement pump is defined by the cartridge body. The saturated bicarbonate solution is drawn from a reservoir on the dialysis machine. The solution is delivered to the pump via a bicarbonate inlet channel 105 and three-way valve 106.

The action of drawing the water into the pump chamber by means of applying a negative pressure to the outer surface of the first membrane 20 generates a turbulent flow within the pump chamber which causes the sterile water and bicarbonate solution to be mixed thoroughly within the pump chamber. Accordingly, at the point where the bicarbonate pump inlet valve 112 is closed, and the outlet valve 114 opens in order to drive a solution from the pump chamber, a thorough homogeneous mixing has been achieved.

The bicarbonate and water solution is pumped out of the pump chamber via a pump exit 116 from which it flows past the pump outlet valve 114 and into a water-bicarbonate solution reservoir 118. The volume of the water-bicarbonate reservoir 118 is approximately four times the volume of the bicarbonate pump chamber and performs two functions. Firstly, it further ensures that the mixture is homogenous, and secondly acts as a fluid buffer within the dialysate solution flow path, the purpose of which will be described in further detail shortly.

The bicarbonate solution reservoir 118 is provided with a conductivity sensing probe 120 and a temperature sensing probe 122, an upper level sensor 124 and a lower level sensor 126.

The conductivity and temperature sensor probes are provided to contact with conductivity and temperature sensors in the dialysis machine. The measurements are used to deduce the concentration of the water-bicarbonate solution in the reservoir 118. The reservoir also acts as buffer to allow for the various system pumps being out of phase. Accordingly, the level in the reservoir is able to rise and fall thereby averaging out pressure spikes in the system.

From the water-bicarbonate reservoir 118, the solution is drawn into an acid pump 128 past an open acid pump inlet valve 130. Coupled to the acid pump 128 is an acid pump outlet valve 132. The purpose of the acid pump 128 is to introduce a small volume of acid solution base into the water-bicarbonate solution. This process is achieved using the same valving and pumping methodology as employed for the bicarbonate pump 108. Specifically, a second chamber 107 is provided for receiving the plunger of a second positive displacement pump. A volume of acid solution base is thereby dispensed down a acid inlet channel 109 to a second 3-way valve 111. Under the action of the pump 128, water-bicarbonate solution is drawn into the pump chamber. The acid solution base is injected into the pump by a second positive displacement pump. The fluids are thoroughly mixed in the turbulent flow within the pump chamber before being dispensed passed the outlet valve 132 into a water bicarbonate-acid reservoir 138.

The water-bicarbonate-acid reservoir 138 is provided with a conductivity sensing probe 144 and a temperature sensing probe 146, an upper level sensor 140 and a lower level sensor 142, in common with the water-bicarbonate reservoir 118.

From the water-bicarbonate-acid reservoir 138, the solution flows through a reservoir exit 147 (see FIG. 7) into a flow balance inlet channel 148. The solution is thereby delivered to the flow balancer 150.

The purpose of the flow balancer 150 is to ensure that the volume of dialysate solution pumped into the dialyser is the same as that withdrawn from the dialyser 80. The purpose of matching the flow into and out of the dialyser is to match the osmotic potential of the dialysate solution within the dialyser to the osmotic potential of the blood. This ensures that the volume of the fluid removed from the blood, or transferred to the blood, can be carefully controlled. This is critical to ensuring that the patient is not hydrated or dehydrated to a dangerous extent during the dialysis treatment.

The flow balancer 150 is provided with a first flow balance pump 152 and a second flow balance pump 154. The first and second flow balance pumps 152, 154 have a similar mode of operation to the blood pump 60, and the mixing pumps 108, 128. However, the flow path for delivering fluid to each of the flow balance pumps 152, 154 is rather more complex due to the way in which the flow balancer 150 achieves the controlled fluid flow input and output from the dialyser 80.

In principal, the flow balancer 150 operates by using the first flow balance pump 152 to pump dialysate solution into the dialyser, and the second flow balance pump 154 to withdraw the dialysate solution from the dialyser, for a period of time, before switching the second flow balance pump 154 to pump dialysate solution into the dialyser, and the first flow balance pump 152 withdrawing dialysate solution from the dialyser. The purpose of this mode of operation is to eliminate the effect of manufacturing tolerances in generating a mismatch in the volume of the pump chamber in each of the flow balance pumps 152, 154. For example, were the first flow balance pump 152 used permanently to pump dialysate solution into the dialyser, and the second flow balance pump 154 used to withdraw dialysate solution from the dialyser, then over a period of time even the very small discrepancy in the pump chamber volume of the pumps would lead to a dangerous imbalance in the volume of dialysate solution being pumped into, and withdrawn from, the dialyser.

By switching the first and second flow balance pumps 152,154, any errors in the chamber volume are averaged over time, thereby ensuring a balance in the flow across the dialyser.

In selective fluid communication with the first flow balance pump 152 are a first flow balance pump first inlet valve 156, a first flow balance pump second inlet valve 158, a first flow balance pump first outlet valve 160 and a first flow balance pump second outlet valve 162. Similarly, in selectable fluid communication with the second flow balance pump 154 are a second flow balance pump first inlet valve 164, a second flow balance pump second inlet valve 166, a second flow balance pump first outlet valve 168 and a second flow balance pump second outlet valve 170.

The first mode of operation of the flow balancer 150 will now be described in detail. In the first mode of operation, the first flow balance pump first inlet valve 156, first flow balance pump second outlet valve 162, second flow balance pump second inlet valve 166 and second flow balance pump first outlet valve 168 are all held in the closed position by the dialysis machine applying a positive pressure to the outside surface of the first membrane 20 in the region of each of the valves. Accordingly, the first mode of operation the second flow balance pump 154 is operated to pump dialysate solution into the dialyser, and the first flow balance pump 152 is operated to withdraw dialysate solution from the dialyser.

With the first flow balance pump first inlet valve 156 in the closed position, dialysate solution passing out of the bicarbonate acid reservoir 138 flows past the first flow balance pump first inlet valve 156 along a flow balance inlet channel 148. The dialysate solution then passes from the lower surface 18 to upper surface 16 via an aperture 172. With the second flow balance pump first inlet valve 164 in its open position, the second flow balance pump 154 is able to draw a volume of dialysate solution into the pump chamber under the action of the dialysis machine generating a negative pressure on the outward facing surface of the first membrane 20.

As soon as the second flow balance pump 154 is at full capacity, the second flow balance pump first inlet valve 164 is closed, and the second flow balance pump second outlet valve 170 is opened. The pump 154 is then actuated to discharge the dialysate solution through an aperture 174 and the dialysate solution then flows along channel 176 as shown in FIG. 10. The dialysate solution then passes through an endotoxin filter 178 before passing through a dialyser output port 180 via channel 182.

Referring now to FIG. 6, from the dialysate outlet port 180, dialysate solution passes along a dialysate inlet pipe 180 before passing along the dialyser 80 from top to bottom as shown in FIG. 9. In order to return the dialysate solution from the dialyser 80 to the pumping portion 12, a dialysate outlet pipe 184 carries dialysate solution to a dialysate inlet port 186. Upon return to the pumping portion 12, the dialysate solution passes through a colour sensor portion 188 in order to allow a colour sensor arranged on the dialysis machine to interrogate the dialysate solution to detect for blood leakage into the dialysate solution within the dialyser 80. On exit from the colour sensor portion 188, the dialysate solution passes through aperture 190 and from there into a flow balance return channel 192.

Since the second flow balance pump second inlet valve 166 is closed, the dialysate solution flows past aperture 194 towards the first flow balance pump second inlet valve 158. With the valve 158 in the open position, the first flow balance pump 152 is able to draw in to the pump chamber a volume of dialysate solution through the inlet valve 158 under the action of a positive pressure generating by the dialysis machine on the outwardly facing surface of the first membrane 20. The first flow balance pump second inlet valve 158 then closes, the first flow balance pump first outlet valve 160 opens, and the pump 152 drives the dialysate solution from the fluid chamber through the outlet valve 160. The outlet valve 160 is then closed, the inlet valve 158 opened and the pump 152 driven to draw in a further volume of dialysate solution ready for dispensing in the next pump cycle.

Having been delivered past the outlet valve 160, the dialysate solution flows through aperture 196 since the second flow balance pump first outlet valve 168 is closed during the mode of operation. The dialysate solution then passes through an ultrasonic flow sensor 198 which will be described in further detail shortly, before exiting the dialysis cartridge 10 by way of dialysate solution drain 200.

In the second mode of operation, the roles of the first and second flow balance pumps 152, 154 are reversed. In other words, the first flow balance pump second inlet valve 158 and first flow balance pump first outlet valve 160 are held closed whilst the first inlet valve 156 and second outlet valve 162 are operated to control the flow of Dialysate solution into and out for the valve chamber. Similarly, with reference to the second flow balance pump 154, the second flow balance pump first inlet valve 164 and second flow balance pump second outlet valve 170 are held in a closed position whilst the second flow balance pump second inlet valve 166 and second flow balance pump and first outlet valve 168 are operated to control the flow of the acid solution into and out of the pump chamber.

The technique of flow balancing, as described above, is provided to ensure that exactly the same volume of dialysate solution is pumped into the dialyser 80 as is removed from it. However, in certain dialysis treatments there is a requirement to either remove excess fluid from the blood, or to transfer fluid back into the blood. This is achieved by the process of ultra-filtration in which the flow balance circuit is placed slightly out of balance by either introducing or removing a small volume of liquid to or from the diayslate solution. In the dialysis cartridge of the present invention this is achieved by an ultra-filtration three-way valve 206 which acts in combination with a positive displacement pump received in chamber 208 on the cartridge. This combination of three-way valve and positive displacement pump is identical to that used to introduce the bicarbonate solution into the bicarbonate pump 108. The positive displacement pump plunger is received within the chamber 208 and is positioned by a drive, for example a stepper motor, on the dialysis machine.

The cartridge 10 has a drainage channel 202 for draining excess fluid from the water-bicarbonate reservoir 118 and the water-bicarbonate-acid reservoir 138. The drainage channel carries excess fluid from the reservoirs 118, 138 and dumps the fluid to drain via a drainage port 204 which is in fluid communication with a drainage port in the dialysis machine.

Accordingly, the dialysis cartridge 10 provides two distinct flow paths, firstly for blood, and secondly for dialysate solution. The provision of an upper surface 16 and a lower surface 18, with apertures therebetween allows the transfer of fluid from the outwardly facing surface of the upper surface to be on the facing surface of the lower surface. The blood flow path and the dialysate solution flow path are maintained discrete from one another by upstanding walls extending from the upper surface and lower surface. The outer surface of the upstanding walls abuts a deformable membrane in order to seal the flow path.

It will be appreciated that the apertures provided in the first and second cartridge bodies 16, 18 allow for the most convenient packaging of the various cartridge features. It is clear that this feature provides a distinct advantage over cartridges which define all of the flow channels on only one side of the cartridge.

In an alternative embodiment of cartridge, the arterial blood bubble trap 34 and venous blood bubble trap 86 have a collapsible element in the form of a concertina section of plastic material so as to limit the area of blood/air interface. This is particularly advantageous in that the reduced blood/air interface reduces the risk of clotting and/or separation of the blood.

A further alternative feature of the bubble trap is to replace the hydrophilic membrane 94 with a membrane pump similar to the blood pump 60. Accordingly, instead of air being added or removed to the bubble trap by way of the transfer of air across the hydrophilic membrane, the transfer of air can be achieved by the displacement of the membrane by the application of either a positive or negative pressure on the outwardly facing surface of the membrane. Furthermore, the extent of actuation of the membrane could be monitored in order to detect where an excessive volume of air is either being added to the reservoir or removed from the reservoir.

In a further alternative embodiment, each of the valves, for example 48, 106, 112, 114, 164 etc are provided with rigid disks which have the diameter equal to or slightly greater than the diameter of the inner upwardly standing wall. The rigid disk is arranged between the inner upwardly standing wall and the membrane. The purpose of the rigid disc is to minimise the deformation required in the membrane in order to seal the valve. In other words, the membrane acts on the rigid disc which in turn forms a valve seat on the inner upwardly standing wall. The result of the reduced deformation of the membrane is that the transient shock waves generated in the valve by virtue of the switching between open and closed is reduced since the valve is closed at a lower peak pressure than would be necessary if the rigid disc were not present. A further benefit in addition to the reduction in pressure spiking observed in the valve body is the reduced blood damage achieved by smoother operation of the valve between its open and closed state.

Referring now to FIG. 10, the positive displacement pump and three-way valve on the current invention are shown schematically in further detail. The three-way valve is indicated generally at 106. It will be appreciated that the three-way valve 106 is identical to the valve in communication with the pump 128 and the ultra-filtration valve 206. The detailed description of three-way valve 106 therefore applies equally to the other two three-way valves provided on the dialysis cartridge.

The bicarbonate mixing pump 108 is connected via a fluid line to an output 250 of the three-way valve 106. The three-way valve also has a reservoir inlet 252 and a pump inlet 254. The reservoir inlet 252 is connected to a bicarbonate solution reservoir 255. The reservoir 255 is provided on the dialysis machine, or attached thereto, and does not form part of the cartridge itself. The positive displacement pump is indicated generally at 258. The positive displacement pump includes a pneumatic cylinder 260 which drives a piston arm 262 in a reciprocating manner. At the opposite end of the piston arm to the piston cylinder is a plunger 264 which acts within the cartridge chamber 104 (see FIG. 10).

On the return stroke indicated at A in FIG. 10, the plunger 264 is moved within the chamber 104 to draw in to the chamber a measured volume of dialysate solution from the bicarbonate solution reservoir 255. This transfer of fluid is achieved by the closure of the three-way valve output 250, with the reservoir inlet and pump inlet 252, 254 remaining open. The piston arm 262 is withdrawn in direction A until an abutment 268 provided on the piston arm 262 comes into contact with a moveable end stop 270.

Upon the abutment 268 hitting the moveable end stop 270, the pneumatic cylinder 268 is driven in direction B in order to dispense the dialysate solution from the chamber 104 into the bicarbonate mixing pump 108. This transfer of fluids is achieved by the closure of the reservoir inlet 252, and the opening of the three-way valve output 250. The pneumatic cylinder 260 drives the piston ring 264 in direction B until the piston ring abuts the extreme left hand end of the chamber 104. Accordingly, by reciprocating the movement of the cylinder piston arm 262 in a known manner, a quantity of bicarbonate solution is repeatedly dispensed into the bicarbonate mixing pump 108. Furthermore, by adjusting the position of the removable end stop 270, the volume of fluid dispensed can be accurately set. The moveable end stop 270 is positioned by a stepper motor or similar accurate positioning drive system.

The advantage of this system is that the pneumatic cylinder 260 provides the speed of the reciprocating movement required to deliver discrete volumes of fluid into the mixing pump 108 at the required rate. A stepper motor which is extremely accurate but not able to provide the speed reciprocation required, is therefore only used to set the dispense volume of fluid by positioning the moveable end-stop accurately.

It will be appreciated that the bicarbonate mixing pump 108, three-way valve 106, and chamber 104 are provided on the cartridge. However, the remainder of the components described in respect of FIG. 10 is provided on the dialysis machine. Importantly therefore, the pneumatic cylinder, stepper motor and moveable lens stop are provided on the machine, not the cartridge.

It will be appreciated that the cartridge of the current invention provides the significant advantage of delivering a homogenous mix of dialysis solution on each and every stroke of the first and second flow balance pumps 152, 154. This feature is critical to delivering a stable dialysis treatment. Furthermore, all of the fluid pathways, pumps and valves required to achieve a homogenous mix are arranged on the cartridge itself. This provides significant advantage since the cartridge contains all of the fluid pathways.

It is conceivable within the scope of the invention that where the provision of a membrane is not necessary to contain flow within a channel, it is conceivable within the scope of invention that such a section of membrane could be removed from the dialysis cartridge 10 following the application of the membrane sheet on to the outwardly facing surface of the cartridge.

Additionally, it is conceivable within the scope of invention that certain sections of flow channel may be strengthened for example, by the thickening of the upwardly standing walls, in order to reduce any flexing in the flow channels resulting from the varied hydrostatic pressure in the fluids.

FIG. 11 shows an alternative embodiment of dialysis portion 312 to that shown in FIGS. 3 to 9. The dialysis portion has a dialyser 314 which is inserted into a first recess 316 and a second recess 318 as shown in FIG. 12. The dialyser 314 is first inserted into the first recess 316 before being rotated towards the dialysis portion and subsequently inserted into the second recess 318. The dialyser 314 is then moved in direction D as shown in FIG. 13 in order to lock the dialyser in place. The locking in place also seals the dialyser 314 against manifolds 320, 320 in order to provide blood access along blood channels 324, 326 and dialysate access along channels 328, 330.

The embodiments above describe a cartridge onto which a bicarbonate solution is delivered from the dialysis machine. In an alternative embodiment, the cartridge is provided with a bicarbonate cartridge 400 as shown in FIG. 14. The cartridge contains a volume of bicarbonate through which is passed sterile water from the sterile water supply which is delivered to the cartridge. The water passes into the bicarbonate cartridge 400 via an inlet 402, passes through the bicarbonate so as to saturate the water with bicarbonate. Bicarbonate solution therefore exits the cartridge 400 through an outlet 404.

In FIG. 15 the bicarbonate cartridge 400 is shown with an adapted portion of dialysis cartridge 10'. The cartridge 10' is adapted to receive plugs 406, 408 in order to secure the fluid connection between the dialysis cartridge 10' and the bicarbonate cartridge. To insert the bicarbonate cartridge 400 onto the dialysis cartridge 10", the plugs 406, 408 are inserted into apertures 410, 412 respectively before the bicarbonate cartridge is moved downwardly in direction B in order to engage the plugs 406, 408 in apertures 414, 416.

In FIG. 16 an alternative heparin reservoir 500 is shown as an alternative to the syringe 71. The reservoir 500 forms part of an adapted dialysis cartridge 10". The reservoir has an outlet 502 which delivers the anticoagulant drug into the blood line by way of a positive displacement pump (not shown for clarity). The reservoir has a deformable sack 504 which contains the anticoagulant drug and a spring 506 which maintains a positive pressure in the sack 506.

The invention claimed is:

1. A disposable dialysis cartridge for use in a hemodialysis machine having a dialyser, the cartridge comprising:
    at least an isolated dialysate flowpath at least partly formed on a surface of the cartridge and configured for delivering a flow of dialysate solution through a dialyser, the dialysate flow path including:
        a sterile water inlet which admits sterile water onto the cartridge from a dialysis machine;
        a first mixing pump having a pump chamber which receives a predetermined volume of sterile water, and
        a dispenser which dispenses into the pump chamber a predetermined volume of a first dialysate solution base,
    wherein the first mixing pump is operable to form a homogeneous mixture of sterile water and first dialysate solution base and pump the homogeneous mixture out of the pump chamber.

2. The disposable cartridge of claim 1, including a regenerative filter, the dialysate flow path being in a recirculating dialysate loop that includes the dialyser and the regenerative filter.

3. The disposable cartridge of claim 1, including a waste fluid outlet, the dialysate flow path being in a continuous dialysate line that includes the sterile water supply inlet from the hemodialysis machine, the dialyser and the waste fluid outlet, the waste fluid outlet being downstream from the dialyser.

4. The disposable cartridge of claim 1, wherein the cartridge includes the dialyser or is adapted to be attachable to the dialyser.

* * * * *